(12) United States Patent
Heidschmidt et al.

(10) Patent No.: US 10,722,677 B2
(45) Date of Patent: Jul. 28, 2020

(54) ANESTHETIC EVAPORATOR AND WICK FOR AN ANESTHETIC EVAPORATOR

(71) Applicant: Drägerwerk AG & Co. KGaA, Lübeck (DE)

(72) Inventors: Michael Heidschmidt, Lübeck (DE); Klaus Radomski, Lübeck (DE); Thomas Lutter, Lübeck (DE); Franz Mair, München (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1019 days.

(21) Appl. No.: 14/950,390

(22) Filed: Nov. 24, 2015

(65) Prior Publication Data

US 2016/0151600 A1  Jun. 2, 2016

(30) Foreign Application Priority Data

Nov. 28, 2014 (DE) .................. 10 2014 017 675

(51) Int. Cl.
*A61M 16/18* (2006.01)
*A61M 11/04* (2006.01)

(52) U.S. Cl.
CPC ........... *A61M 16/18* (2013.01); *A61M 11/042* (2014.02); *A61M 2205/3368* (2013.01)

(58) Field of Classification Search
CPC ................. A61M 11/042; A61M 16/18; A61M 2205/3368; A61M 11/044; A61M 11/048; A61M 11/045; A61M 16/00; A61M 16/10; A61M 2205/3372; A61M 16/167; A61M 16/168; A61M 11/041; A61M 16/1045; A61M 16/1075; A61M 16/109; A61M 16/147; A61M 16/16; A61M 16/162; A61M 2016/1035; A61M 2205/3653; A61M 16/22; A61M 2202/0208; A61M 16/104;

(Continued)

(56) References Cited

U.S. PATENT DOCUMENTS 3,671,024 A * 6/1972 Breiling ................ A61M 16/18
128/203.14
4,075,297 A * 2/1978 Seidel ................... A61M 16/18
128/204.13

(Continued)

FOREIGN PATENT DOCUMENTS

DE         101 34 284 C1    11/2002
DE     10 2008 045 081 A1    3/2010
EP          1 530 980 A1     5/2005

*Primary Examiner* — Kendra D Carter
*Assistant Examiner* — Brian M. Booker
(74) *Attorney, Agent, or Firm* — McGlew and Tuttle, P.C.

(57) ABSTRACT

A wick (12) includes a porous molding, which has a plurality of air ducts (26) extending in the vertical direction, a plurality of upper deflection chambers (28), which connect each a first air duct pair (29) of the plurality of air ducts (26) to one another, and a plurality of lower deflection chambers (30), which connect each a second air duct pair (31) of the plurality of air ducts (26) to one another. The two air ducts (26) of the second air duct pairs (31) are each associated with different first air duct pairs (29). An anesthetic evaporator (10) includes a housing (14, 16), which receives the wick (12), so that the vertical air ducts (26) and the upper and lower deflection chambers (28, 30) form an air flow duct between the air inlet (22) and the air outlet (24).

19 Claims, 5 Drawing Sheets

(58) Field of Classification Search
CPC ............ A61M 2230/437; A61M 16/01; A61M
16/0833; A61M 16/186; A61M
2016/0027; A61M 2016/0039; A61M
2016/1025; A61M 2202/0007; A61M
11/00; A61M 11/002; A61M 11/02;
A61M 11/04; A61M 11/047; A61M
15/0021; A61M 15/0045; A61M 15/0048;
A61M 15/065; A61M 15/008; A61M
15/0081; A61M 15/06; A61M 16/009;
A61M 16/0093; A61M 16/04; A61M
16/08; A61M 16/0841; A61M 16/0858;
A61M 16/1015; A61M 16/1055; A61M
16/107; A61M 16/12; A61M 16/14;
A61M 16/164; A61M 16/183; A61M
2016/0021; A61M 2016/003; A61M
2016/0036; A61M 2016/103; A61M
2202/0283; A61M 2202/03; A61M
2202/064; A61M 2205/123; A61M
2205/3375; A61M 2205/36; A61M
2205/3606; A61M 2205/364; A61M
2205/3673; A61M 2205/50; A61M
2205/505; A61M 2205/8268; A61M
2230/432; F28D 15/0266; F28D 15/0275;
F28D 15/046; F28D 9/005; F28D 15/02;
F28D 21/0003; B01B 1/005; B01F 3/022;
F24F 11/30; F24F 2110/00; F24F 6/043;
F24F 6/10; F24F 2003/1689; F24F 6/00;
F24F 6/025; F24F 6/08; F24H 1/00;
F24H 1/121; F24H 1/202; F24H 9/1827;
Y10S 165/398; Y10S 165/907; Y10S
261/34; Y10S 261/65; Y10T 137/7358;
Y10T 29/49861; Y10T 428/24314; Y10T
137/1963; Y10T 137/86743; Y10T
29/49002; A01M 1/2033; A01M 1/2044;
A61J 9/122; A61J 9/127; A61L 2209/11;
A61L 2209/135; A61L 2400/12; A61L
2420/02; A61L 31/16; A61L 9/03; A61L
9/037; B01J 19/0093; B01J 2219/00783;
B01J 2219/00822; B01J 2219/00835;
B01J 2219/00873; B01J 2219/00891;
B01J 2219/00905; B01J 2219/00995;
B01J 19/2475; B01J 2219/00162; B01J
23/40; B01J 37/0238; B01J 8/009; B01D
19/0031; B01D 3/00; B01D 53/002;
B01D 5/0003; B01D 53/22; B01D
53/326; B01L 3/5027; B01L 3/50273;
C01B 2203/0233; C01B 2203/066; C01B
2203/0805; C01B 2203/0833; C01B
3/384; F28F 2260/02; F28F 13/187; F28F
2265/26; F28F 27/02; H05B 2203/021;
H05B 1/0244; H05B 1/0283; H05B 3/26;
H05B 3/42; Y02C 20/10; Y02C 20/30;
A61F 2240/001; A61F 2250/0068; A61K
9/0092; B05B 7/1686; B65B 29/10; C02F
1/4618; C02F 1/4672; C02F 1/78; C02F
2001/46128; C02F 2001/46142; C02F
2001/46166; C02F 2101/30; C02F
2201/46115; C02F 2201/46195; C02F
2201/782; C02F 2303/04; C06B 33/00;
C06B 45/14; C09K 5/18; C25B 13/02;
C25B 1/13; C25B 9/08; F16T 1/00; F22B
1/284; F23B 2900/00003; F23C
2900/99008; F24V 30/00; F25B 41/06;
G01K 5/32; G01N 33/0006; G05D 22/02;
H01G 4/33; H01G 9/0032; H01G 9/07;
H01G 9/15; H01M 2300/0082; H01M
4/0428; H01M 4/64; H01M 8/0202;
H01M 8/04291; H01M 8/1007; H01M
8/1023; H01M 8/1039; H01M 8/1065;
H01M 8/186; H05K 1/092; H05K 1/162;
H05K 2201/0116; H05K 2201/0179;
H05K 2201/09763; H05K 2203/1131;
Y02E 20/346; Y02E 60/528; Y02P 70/56
See application file for complete search history.

(56) References Cited

U.S. PATENT DOCUMENTS

| | | | | |
|---|---|---|---|---|
| 4,225,542 | A * | 9/1980 | Wall | A61M 16/1075 128/203.12 |
| 4,461,735 | A * | 7/1984 | Wirt | F24F 6/08 128/204.13 |
| 4,618,462 | A * | 10/1986 | Fisher | F24F 6/00 236/44 C |
| 5,490,500 | A * | 2/1996 | Reichert | A61M 16/18 128/200.21 |
| 6,785,247 | B1 * | 8/2004 | Lee | H04W 52/143 370/252 |
| 8,496,003 | B2 * | 7/2013 | Kleinschmidt | A61M 16/18 128/204.13 |
| 2005/0133030 | A1 * | 6/2005 | Fiedorowicz | A61M 16/18 128/204.13 |
| 2009/0090472 | A1 * | 4/2009 | Radomski | A61M 11/041 159/43.1 |
| 2010/0051028 | A1 * | 3/2010 | Kleinschmidt | A61M 16/18 128/204.13 |
| 2011/0310530 | A1 * | 12/2011 | Laor | B01J 37/0238 361/524 |
| 2013/0269912 | A1 * | 10/2013 | Fetcu | F28D 15/02 165/104.14 |

* cited by examiner

ANESTHETIC EVAPORATOR AND WICK FOR AN ANESTHETIC EVAPORATOR

CROSS REFERENCE TO RELATED APPLICATIONS

This application claims the benefit of priority under 35 U.S.C. § 119 of German Patent Application 10 2014 017675.4 filed Nov. 28, 2014, the entire contents of which are incorporated herein by reference.

FIELD OF THE INVENTION

The present invention pertains to an anesthetic evaporator and to a wick for an anesthetic evaporator with a porous molding.

BACKGROUND OF THE INVENTION

Wicks for anesthetic evaporators, which are manufactured from flexible materials and thus require additional components for shaping, are known from the state of the art.

A dimensionally stable wick for an anesthetic evaporator, which is manufactured from a porous molding and takes in liquid anesthetic from a reservoir by capillary forces, is known from US 2010/0051028 A1. Air flows through a helical air flow duct and absorbs evaporated anesthetic at the wall of the wick. However, such a wick is difficult to manufacture because of its geometry. Since a side wall of the helical air flow duct is formed, moreover, by a component of the housing, strict manufacturing tolerances are necessary for the molding forming the wick.

SUMMARY OF THE INVENTION

An object of the present invention is to provide a wick for an anesthetic evaporator with a simple design and with good evaporation function as well as a corresponding anesthetic evaporator.

A wick according to the present invention for an anesthetic evaporator comprises a porous molding (a porous molded article) with a plurality of air ducts, which extend in the vertical direction and through which a gas flow to be enriched with anesthetic flows. It is essential in this connection that at least two air ducts are provided, which are arranged at least extensively vertically in the installed position of the porous molding, through which the gas flow to be enriched with anesthetic can flow in respective opposite directions. At least one first and one second air duct arranged at least extensively vertically in the installed position of the porous molding are preferably connected in the upper area via a deflection chamber, which is configured as a depression in the molding, and, in addition, the first and/or second air duct is connected to a third air duct in the lower area via a deflection chamber, which is configured as a depression in the molding. The deflection chambers ensure that after the wick has been installed, a breathing gas flow or a breathing air flow can flow from an air duct into the air duct connected thereto fluidically via the deflection chamber. Two air ducts connected to one another via a deflection chamber will hereinafter also be called air duct pair, and an air duct may be associated with two air duct pairs, namely, with a first air duct pair, which has a deflection chamber in the upper area, and a second air duct pair, which has a deflection chamber in the lower area.

According to a special embodiment of the present invention, the wick has a plurality of upper deflection chambers, which connect each a first air duct pair of the plurality of air ducts with one another, and a plurality of lower deflection chambers, which connect each a second air duct pair of the plurality of air ducts with one another. The two air ducts of the second air duct pair are each associated with different first air duct pairs.

The vertical air ducts and upper and lower deflection chambers form a simple geometry without undercuts, as a result of which simple manufacture is made possible. Due to the vertically extending air ducts being connected via the upper and lower deflection sections, an air flow duct can be formed for an anesthetic evaporator, which said air flow duct is formed completely by the wick with the exception of the axial end faces, as a result of which the mode of construction of a corresponding anesthetic evaporator is simplified. Moreover, a large evaporation surface is made available in this way along the air flow duct, as a result of which good function of the anesthetic evaporator is guaranteed.

The porous molding preferably has, furthermore, a plurality of recesses, which are arranged between the air ducts. This makes possible a large surface for heat transfer to the wick, for example, via heat transfer elements of a housing of an anesthetic evaporator.

The recesses preferably extend from the upper end of the molding downwardly in the vertical direction. This makes possible, for example, the simple assembly of heat transfer elements of an anesthetic evaporator at the wick in the vertical direction.

According to a preferred embodiment, the recesses do not extend in the vertical direction from the upper end of the molding to the level of the lower deflection chambers. For example, the recesses may extend over ½ of the length of the vertical air ducts to ⅞ of the length of the vertical air ducts. Good heat transfer is achieved in this way in the area of the air ducts.

The lower deflection chambers advantageously form a reservoir for liquid anesthetic and extend especially in the vertical direction at least over half the height of the molding. This makes it possible to form a reservoir for liquid anesthetic in the area of the lower deflection chambers, as a result of which a correspondingly long operating time is made possible without refilling. Furthermore, the surface of the wick is enlarged in this way along an air flow duct in an anesthetic evaporator when the anesthetic level is dropping. Cooling effects can thus be compensated during longer operation.

Simple mode of construction of the wick and a correspondingly simple assembly of the anesthetic evaporator are made possible by the molding being formed integrally from a sintered material. The molding may consist, for example, of a sintered plastic, metal, ceramic or glass material.

The present invention pertains, furthermore, to an anesthetic evaporator with a wick, especially as described above. The anesthetic evaporator according to the present invention has a porous molding, which has a plurality of air ducts extending in the vertical direction in the installed position of the molding; a plurality of upper deflection chambers, which connect two air ducts each in the upper area to one another; a plurality of lower deflection chambers, which connect each one of the two air ducts connected by the upper deflection chamber to another air duct; a housing, which accommodates the wick; as well as an air inlet and an air outlet, which are arranged such that the vertical air ducts and the upper and lower deflection chambers form an air flow duct for gas to be enriched with anesthetic between the air inlet and the air outlet.

The wick preferably has a porous molding, which has a plurality of air ducts extending in the vertical direction, a plurality of upper deflection chambers, which connect each a first air duct pair of the plurality of air duct pairs to one another, and a plurality of lower deflection chambers, which connect each a second air duct pair of a plurality of air ducts. The anesthetic evaporator has, furthermore, a housing, which accommodates the wick, an air inlet and an air outlet. The wick, housing, air inlet and air outlet are arranged such that the vertical air ducts and the upper and lower deflection chambers form an air flow duct between the air inlet and the air outlet.

The housing preferably has a pot component, said pot component receiving at least a lower section of the wick and forming a reservoir for liquid anesthetic with the lower deflection chambers.

The housing preferably has a cover component, which has the air inlet and the air outlet. The wick, pot component and cover component are arranged such that the vertical air ducts and the upper and lower deflection chambers form an air flow duct between the air inlet and the air outlet.

The deflection chambers are preferably configured as depressions in the molding, into which the respective air ducts to be connected open. It is conceivable with respect to the upper deflection chambers that these may be arranged at least partially in the cover component.

According to a preferred embodiment, the housing, especially the cover component, has a plurality of heat transfer elements, which are configured to mesh with a plurality of recesses of the wick, said recesses and the heat transfer elements being arranged between the air ducts. Good heat transfer is made possible in this way between the cover component and the wick.

Further features and advantages of the present invention appear from the following description and from the drawings, to which reference is made.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
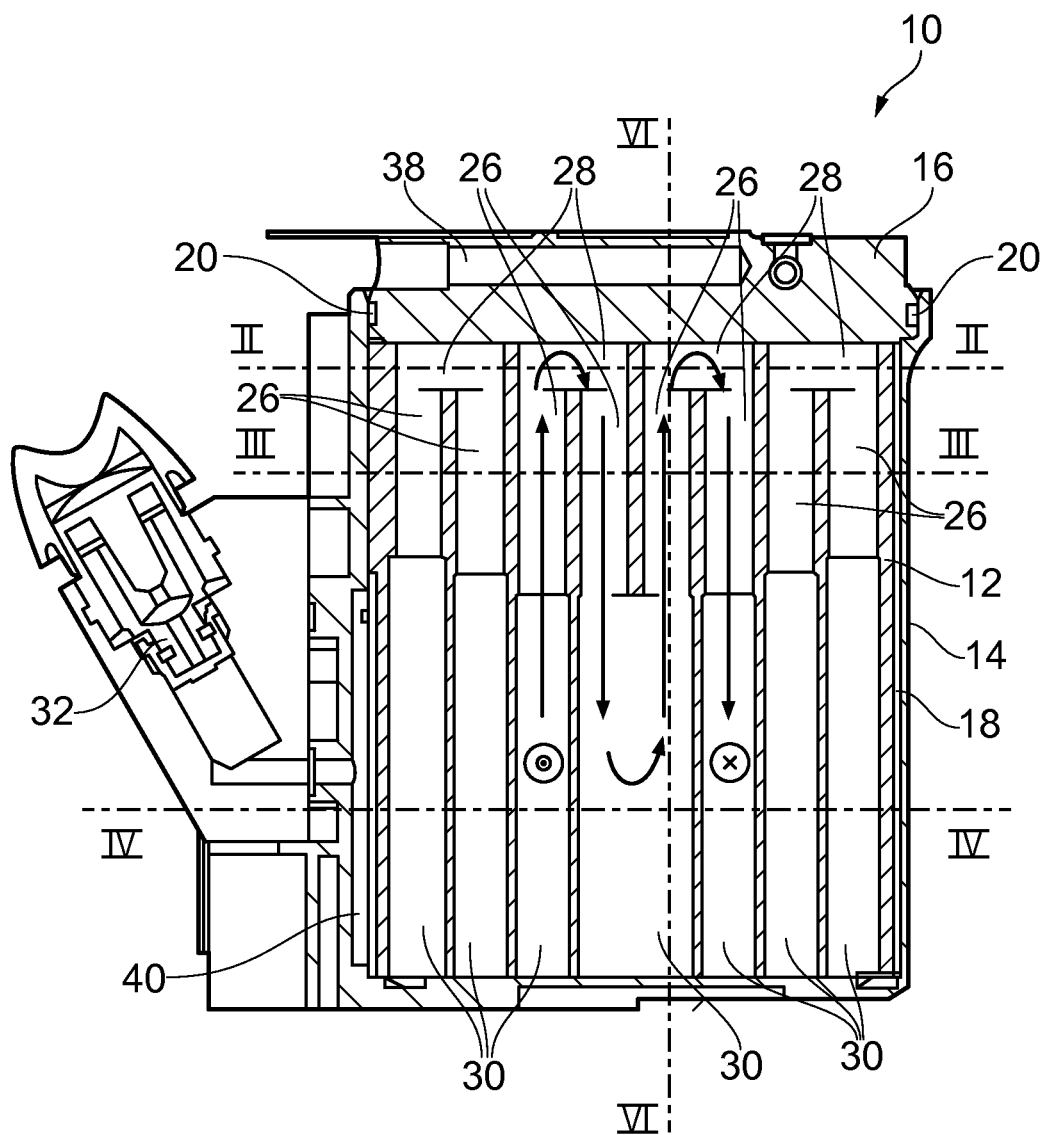
FIG. 1 is a vertical sectional view of an anesthetic evaporator according to the present invention.

Referring to the drawings, FIG. 1 shows a sectional view of an anesthetic evaporator 10 with a wick body (wick) 12, with a pot component 14 and with a cover component 16. The pot component 14 forms a housing for the wick 12 with the cover component 16, the pot component 14 receiving the wick 12 in an inner space 18 in the embodiment being shown. The inner space 18 has an upper opening, which can be closed by the cover component 16, and a sealing element 20 is provided, which seals the upper opening of the inner space 18.

The cover component has an air inlet 22 and an air outlet 24, through which air used for ventilation enters the anesthetic evaporator 10 and leaves same enriched with anesthetic.

A different design of the housing may also be provided, for example, with a vertical division. The air inlet 22 and the air outlet 24 may also be arranged on another part of the housing, for example, the pot component 14 or the wick 12.

Figure 2:
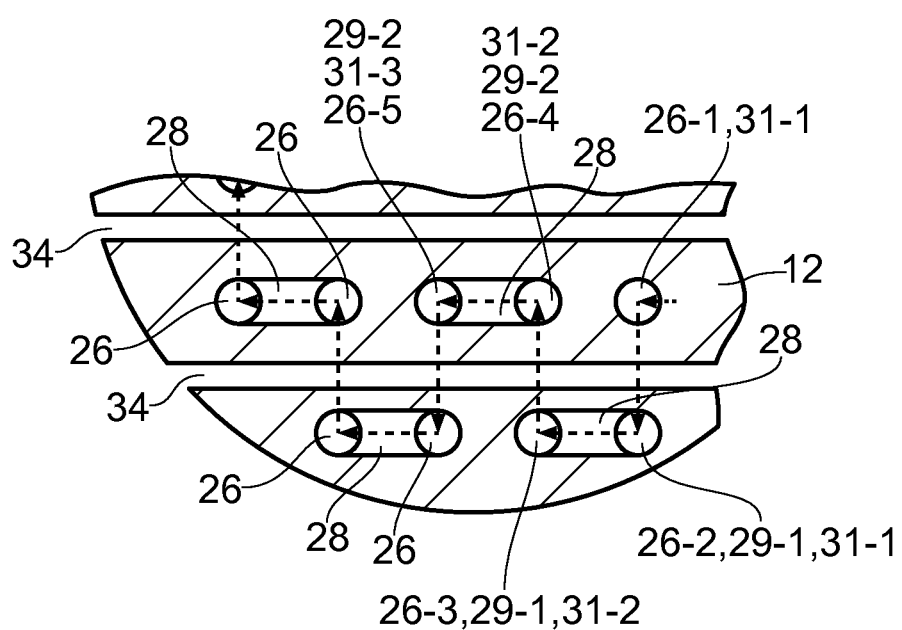
FIG. 2 is a first horizontal sectional view of the anesthetic evaporator from FIG. 1 along section line II-II.
Figure 3:
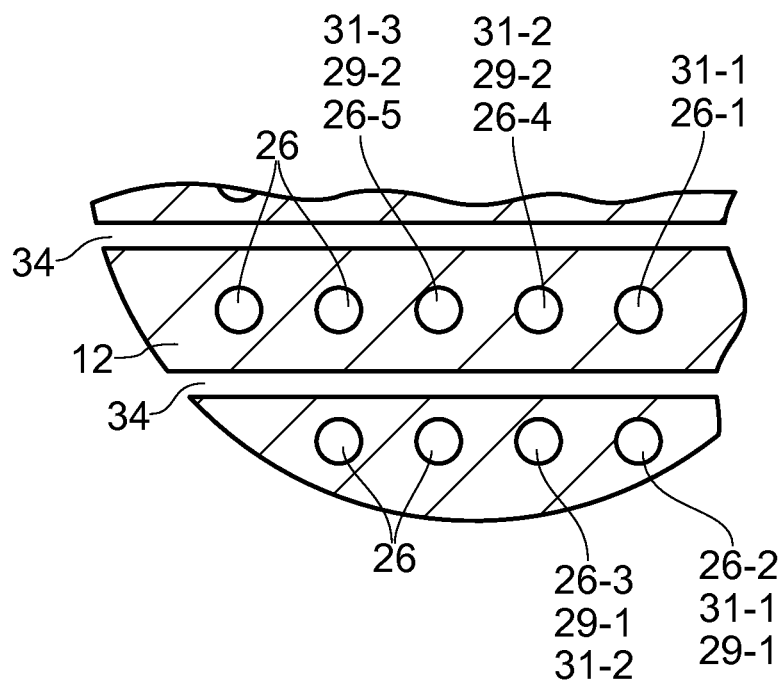
FIG. 3 is a second horizontal sectional view of the anesthetic evaporator from FIG. 1 along section line III-III.
Figure 4:
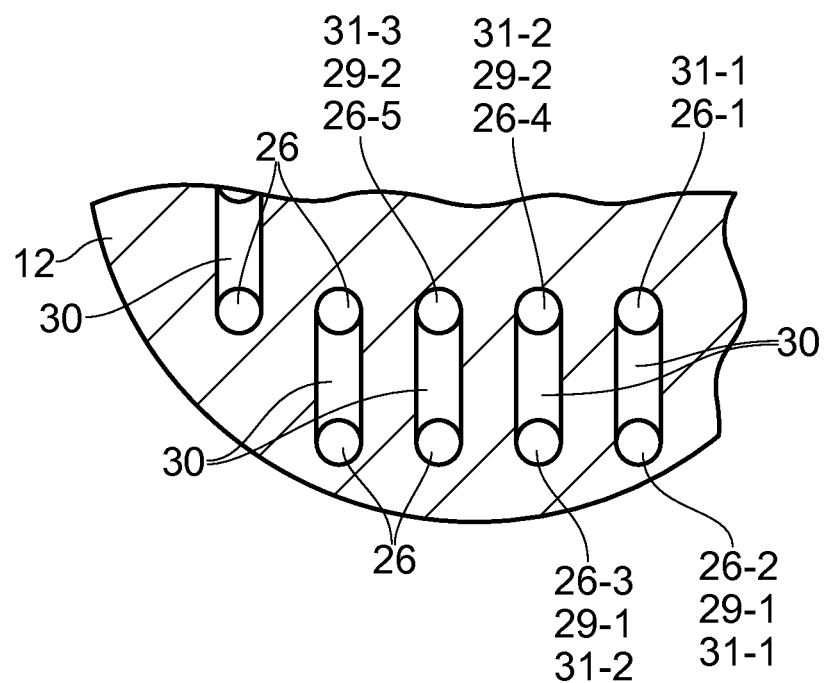
FIG. 4 is a third horizontal sectional view of the anesthetic evaporator from FIG. 1 along section line IV-IV.
Figure 5:
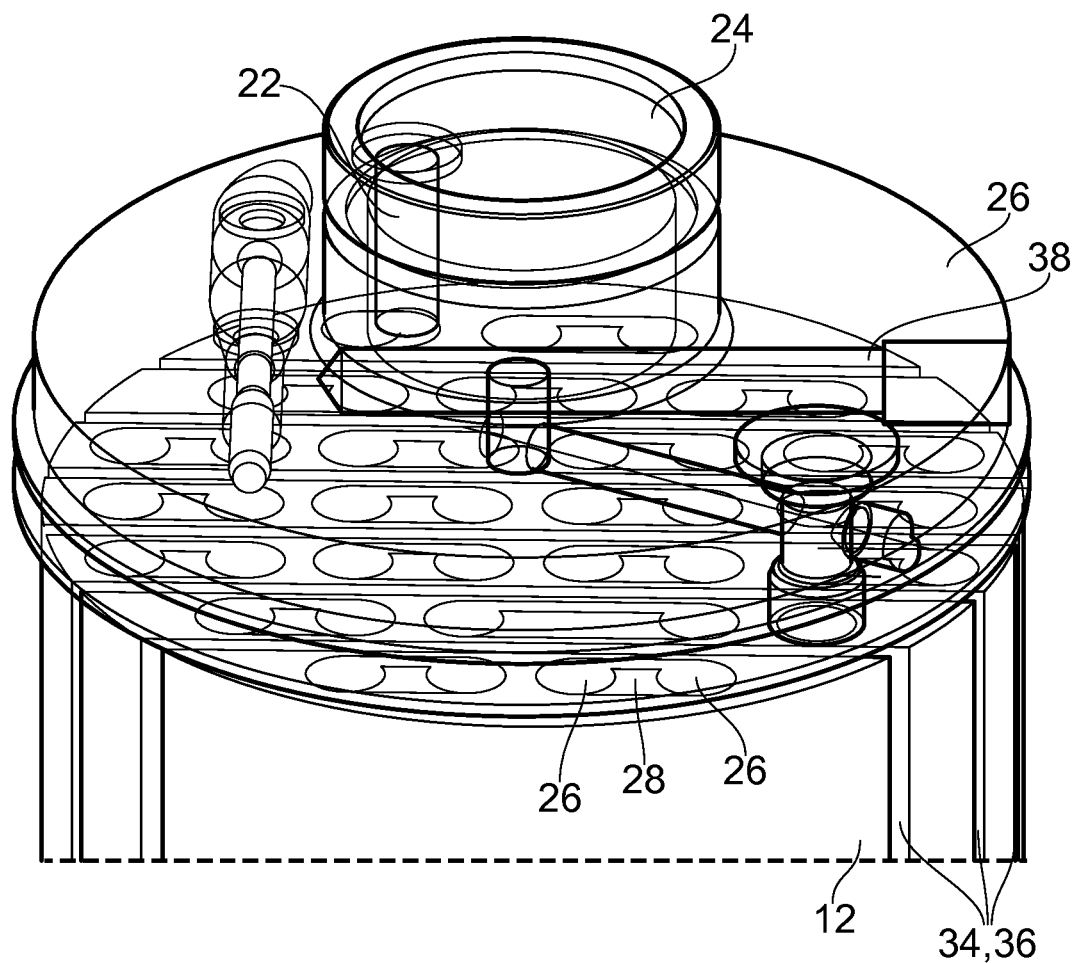
FIG. 5 is a perspective view of the anesthetic evaporator from FIG. 1.
Figure 6:
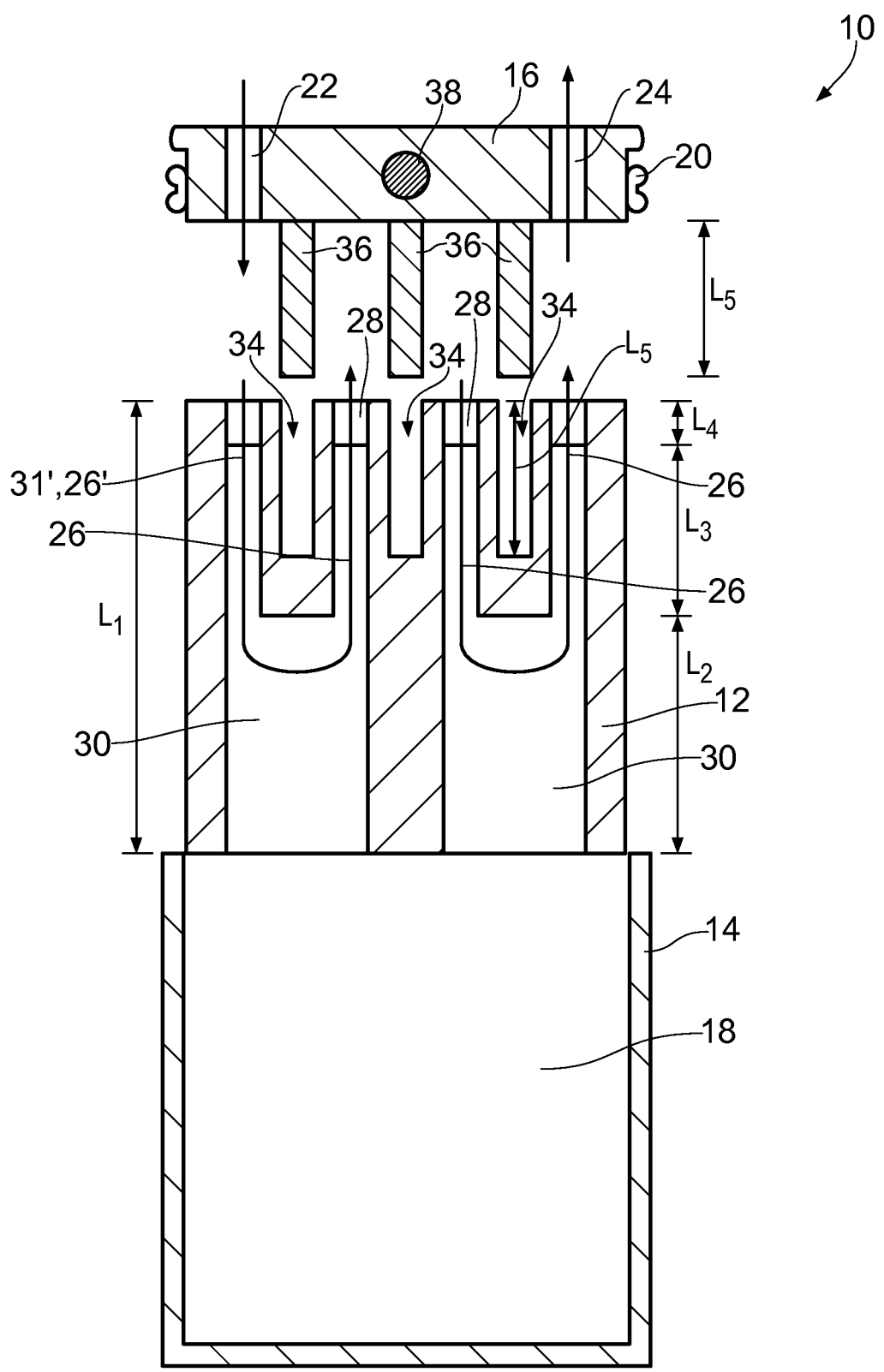
FIG. 6 is a schematic exploded view of the anesthetic evaporator from FIG. 1.

FIGS. 2, 3 and 4 show each sectional views of the wick 12 in the section planes II-II, III-III and IV-IV shown in FIG. 1. FIG. 5 shows a schematic perspective view of the upper section of the anesthetic evaporator 10. FIG. 6 shows a schematic exploded view of a section in the vertical direction corresponding to the section plane VI-VI shown in FIG. 1.

The wick 12 comprises a porous molding with a plurality of air ducts 26 extending in the vertical direction. A plurality of upper deflection chambers 28 connect each a first air duct pair 29 of the plurality of air ducts 26 to one another.

A plurality of lower deflection chambers 30 are provided, the lower deflection chambers 30 connecting each a second air duct pair 31 of the plurality of air ducts 26 to one another. The two air ducts 26 of the second air duct pairs 31 are each associated with different first air duct pairs 29. The air ducts 26 thus extend each between an upper deflection chamber 28 and a lower deflection chamber 30.

As is shown in FIG. 6, the entire height of the wick 12 in the vertical direction is the length $L_1$. The lower deflection chambers 30 extend upward over a length $L_2$ from the lower end of the molding of the wick 12 in the vertical direction. The upper deflection chambers 28 extend downward in the vertical direction over a length $L_4$ from the upper end of the molding of the wick 12. The air ducts extend over a length $L_3$ between the upper and lower deflection chambers 28, 30. The different upper and lower deflection chambers and the air ducts may each have the same lengths, or they may have different lengths.

The radially outer lower deflection chambers 30 are higher than the radially inner lower deflection chambers 30 in the embodiment shown in FIG. 1. This guarantees independence from the position when the anesthetic evaporator 10 is tilted by a certain angle and the anesthetic level is thus higher on one side of the wick than on the other, because no liquid anesthetic will reach the radially outer vertical air duct 26 in this case and the air flow through this is blocked.

The wick 12 forms in this way, together with the outer housing formed by the pot component 14 and the cover component 16, an air flow duct, which guides the air flowing in through the air inlet 22 to the air outlet 24. Exactly one air flow channel, which guides the air from the air inlet 22 via the air ducts 26 and the upper and lower deflection chambers 28, 30 to the air outlet 24, is provided in the embodiment being shown. Provisions may also be made, as an alternative, for the air ducts 26 and the upper and lower deflection chambers 28, 30 to form a plurality of air flow channels, which are connected in series and guide air flows from the air inlet 22 to the air outlet 24.

The vertical air ducts and upper and lower deflection chambers form a simple geometry without undercuts. This makes possible a simple manufacture of the molding of the wick 12. Due to the vertical air ducts being formed completely by the molding itself, it is not necessary to impost high requirements on the manufacturing tolerances.

The upper and lower deflection sections 28, 30 form connections of the vertically extending air ducts 26, so that, together with the housing formed by the pot component 14 and the cover component 16, an air flow duct is formed for air in the anesthetic evaporator 10, which air flow duct is formed completely by the wick 12 with the exception of the axial end faces. Besides a simple design of the wick, a simple design of the other components of the anesthetic evaporator 10, especially of the pot component and the cover component, is possible as well. In addition, this geometry guarantees the formation of a large evaporation surface on the wick walls along the air flow channel, via which the liquid anesthetic can evaporate and be released to the air flowing through. Good function of the anesthetic evaporator 10 is guaranteed in this way and a compact design is made possible.

Together with the pot component 14, the lower deflection chambers 30 form a reservoir for liquid anesthetic. An anesthetic feed valve 32 makes it possible to feed a liquid anesthetic into the pot component 14. The liquid anesthetic can enter through the porous material of the wick 12 and thus it assumes an essentially uniform liquid level in all lower deflection chambers 30. The liquid level may be, for example, at the level of the section line IV-IV. The porous material of the molding of the wick 12 is configured such that the liquid anesthetic rises in the wick 12 due to capillary forces.

The wick 12 is arranged completely in the inner space 18 of the pot component 14 in the embodiment being shown. It is also possible, as an alternative, that only a lower section of the wick 12 is arranged in the inner space 18 and the upper section of the wick 12 is received in a corresponding inner space of the cover component 16.

In the embodiment being shown, the lower deflection chambers 30 extend in the vertical direction over more than half the height $L_1$ of the molding (see FIG. 6). A large reservoir is formed in this way for liquid anesthetic in the area of the lower deflection chambers 30, as a result of which a correspondingly long operation of the anesthetic evaporator 10 is possible without refilling liquid anesthetic.

When the anesthetic level drops in the lower deflection chambers 30, the free surface of the wick 12 becomes larger, so that the release of anesthetic to the air in the air flow duct is improved. Since a plurality of lower deflection chambers 30 are provided and the free surface of the wick 12 is enlarged in each of the deflection chambers 30, an optimal effect can be achieved.

Adverse effects, which reduce the evaporation of anesthetic, e.g., a greater capillary rise of the anesthetic in the wick and cooling effects during longer operation, can be compensated in this way.

The wick 12 is an integral molded wick body, namely formed by a molding of integral design made of a sintered material in the embodiment being shown. The molding is manufactured from a sintered plastic material in the embodiment being shown. A sintered metal, ceramic or glass material may also be provided as an alternative.

As can be seen in FIGS. 2 through 6, the porous molding of the wick 12 has, furthermore, a plurality of recesses 34, which are arranged between the air ducts 26. The recesses 34 are formed each between the second air duct pairs 31 in the embodiment being shown. The recesses 34 extend downward in the vertical direction from the upper end of the molding and have a length $L_5$ in the vertical direction. The length $L_5$ is selected to be such that the recesses 34 do not extend fully to the level of the lower deflection chambers 30 from the upper end of the molding in the vertical direction. For example, the length $L_5$ of the recesses is between ½ the length $L_3$ of the vertical air ducts to ⅞ of the length $L_3$ of the vertical air ducts.

The cover component 16 has, in turn, a plurality of heat transfer elements 36, which are configured to mesh with the recesses 34 of the wick 12. The recesses 34 and the heat transfer elements 36 are arranged between the air ducts 26. Good heat transfer is made possible in this way between the cover component 16 and the wick 12.

In the embodiment being shown, the cover component 16 comprises a heating element 38, which makes it possible to heat the cover component 16. The heat generated by the heating element 38 is transferred via the heat transfer elements 36 to the wick 12 and it thus increases the rate of evaporation of the liquid anesthetic. Cooling of the inner space 18 by the evaporation of the anesthetic can be counteracted in this way and a desired rate of evaporation can be maintained.

The anesthetic evaporator comprises, furthermore, a temperature control/regulation element, which is associated with the heating element 38 and makes it possible to control and/or regulate the temperature of the anesthetic evaporator 10.

The cover component 16 is made of a material with good thermal conductivity in the embodiment being shown and thus it makes possible a good heat transfer between the heating element 38 and the heat transfer element 36. It is also possible that only the heat transfer elements 36 are formed from a material with good thermal conductivity and are in contact with the heating element, while other components of the cover component are manufactured from other, heat-insulating materials.

As an alternative or in addition, provisions may also be made for the cover component 16 to absorb heat from the surrounding area and to transfer it to the wick 12 via the heat transfer elements 36. For example, heat transfer elements, which enlarge the surface of the cover component 16 and thus improve the heat transfer from the surrounding area, may also be provided for this on the outer side of the cover component 16.

The recesses 34 and the heat transfer elements 36 are of a linear design in the embodiment being shown. However, other shapes are also possible; for example, round or polygonal honeycomb-like heat transfer elements 36 and recesses 34, which surround each one of the upper deflection chambers 28, may be provided, as a result of which the sealing of the upper deflection chambers 28 against one another can also be improved.

The arrangement of heat transfer elements 36 and corresponding recesses 34 in the wick 12 makes it possible to enlarge the contact surface between the cover component 16 and the wick 12 and thus to improve the heat transfer, especially in the area of the air ducts 26. In addition, simple assembly of the anesthetic evaporator 10 is made possible by the vertical orientation of the heat transfer elements 36.

To achieve good heat transfer between the heat transfer elements 36 and the wick 12, the recesses 34 are somewhat undersized, so that the side walls of the recesses 34 are exposed to the heat transfer elements 36. It is also possible that the heat transfer elements 36 are configured as elastic elements and are exposed to the side walls of the recesses 34.

The function of the anesthetic evaporator 10 and the course of the air flow in the anesthetic evaporator 10 will be described below on the basis of FIGS. 1 through 6.

When assembling the anesthetic evaporator 10, the wick 12 is inserted into the pot component 14 and the pot component 14 is subsequently closed with the cover component 16.

Liquid anesthetic is introduced into the pot component 14 via the anesthetic feed valve 32 until an intended anesthetic level is reached. The anesthetic is absorbed in the porous material of the molding of the wick 12 due to capillary forces.

To improve the spreading of the liquid anesthetic, an annular space 40 is provided, which extends completely or partially along the circumference of the lower section of the wick 12. The annular space 40 is formed in the embodiment being shown by both a corresponding recess of the pot component 14 and of the molding of the wick 12. However, it is also possible that the annular space 40 is formed only by a recess of the pot component 14 or of the molding of the wick 12. Furthermore, radial ducts, which may be formed by a corresponding recess of the pot component 14 and/or of the molding of the wick 12, may be provided on the underside of the wick 12 for spreading the liquid anesthetic in the radial direction.

A reservoir for liquid anesthetic is formed in this way by the annular space 40 in a region of the lower deflection chambers 30.

Air, used for ventilation, flows into the anesthetic evaporator 10 via the air inlet 22 of the cover component 16. The air ducts 26 and the upper and lower deflection chambers 28, 30 form an air flow duct from the air inlet 22 to the air outlet 24. The air flows first into a first air duct 26-1, which forms with a second air duct 26-2 an air duct pair 31-1. The first air duct 26-1 and the second air duct 26-2 are connected to one another via a lower deflection chamber 30. The air is deflected on the surface of the liquid anesthetic in the lower deflection chamber 30 and flows upward through the second air duct 26-2.

With a third air duct 26-3, the second air duct 26-2 forms, in turn, an air duct pair 29-1, which third air duct 26-3 and second air duct 26-2 are connected to one another via an upper deflection chamber 28. The air is deflected in the upper deflection chamber 28 on the wall of the cover component 16 and flows downward through the third air duct 26-3.

With a fourth air duct 26-4, the third air duct 26-3 forms an air duct pair 31-2, which fourth air duct 26-4 and the third air duct 26-3 are connected to one another via a lower deflection chamber 30.

With a fifth air duct 26-5, the fourth air duct 26-4 forms an air duct pair 29-2, which fifth air duct 26-5 and fourth air duct 26-4 are connected to one another via an upper deflection chamber 28.

Analogously to the first through fifth air ducts, the air flows in the other air ducts up to the air outlet 24 in the cover component 16.

The liquid anesthetic evaporates on the walls of the porous molding of the wick 12 along the air flow duct and passes over into the air used for ventilation through the air flow duct.

The wick 12 cools increasingly during the evaporation of the liquid anesthetic, as a result of which the rate of evaporation decreases. This can be compensated, on the one hand, by an enlarged surface of the wick walls in the lower deflection chambers 30 while the anesthetic level drops.

On the other hand, there is an effective heat transfer from the cover component 16 via the heat transfer elements 36 to the wick 12. Heat from the heating element 38 or from the surrounding area is effectively transferred in this way to the wick 12, especially due to the heat transfer elements 34 being arranged between the vertically extending air ducts 26.

The heating element can be operated in a regulated manner in the embodiment being shown, so that controlled heat can be fed to the wick 12 for the evaporation.

While specific embodiments of the invention have been shown and described in detail to illustrate the application of the principles of the invention, it will be understood that the invention may be embodied otherwise without departing from such principles.

What is claimed is:

1. An anesthetic evaporator wick comprising:
a plurality of heat transfer elements; and
a porous molded wick body defining at least a first air duct and a second air duct passing through the molded wick body from an upper surface side to an opposite lower surface side, in which first air duct and second air duct a gas flow, flowing through the at least first air duct and second air duct is enriched with anesthetic, wherein:
the first air duct and the second air duct are arranged at least extensively vertically in an installed position of the porous molded wick body and through which the gas flow to be enriched with anesthetic can flow in opposite directions;
the porous molded wick body at least partially defines at least one upper deflection chamber configured as a depression in the molded wick body top surface side;
the first air duct and the second air duct are connected in an upper area via the upper deflection chamber;
the porous molded wick body further defines a third air duct;
the porous molded wick body further at least partially defines at least one lower deflection chamber configured as a depression in the porous molded wick body lower surface side;
at least one of the first air duct and the second air duct is connected in a lower area to the third air duct via the lower deflection chamber;
the porous molded wick body further defines a plurality of recesses arranged between the air ducts, each of the recesses extending into the porous molded wick body a distance from a heat transfer element receiving side of the porous molded wick body and receiving one of the plurality of heat transfer elements from the heat transfer element receiving side; and
the heat transfer elements are each configured corresponding to one of the plurality of recesses defined by the molded wick body and extend into said one of the plurality of recesses defined by the molded wick body and mesh with said one of the plurality of recesses defined by the molded wick body to transfer heat from outside the wick body to within the wick body.

2. An anesthetic evaporator wick in accordance with claim 1, wherein the recesses extend downward in a vertical direction from the upper surface side, which is an upper end of the porous molded wick body, to a location spaced from the opposite lower surface side.

3. An anesthetic evaporator wick in accordance with claim 1, wherein the lower deflection chamber forms a reservoir for liquid anesthetic and extends in a vertical direction at least over half a height of the porous molded wick body.

4. An anesthetic evaporator wick in accordance with claim 1, wherein the porous molded wick body is a single piece integral molded structure made from a sintered material.

5. An anesthetic evaporator wick in accordance with claim 1 wherein the porous molded wick body is an integral single piece structure.

6. An anesthetic evaporator wick in accordance with claim 1, in combination with a heating element configured to generate heat, wherein:
the recesses extend from a heat transfer element receiving side of the porous molded wick body, which heat transfer element receiving side is defined by one of the upper surface side and the opposite lower surface side of the porous molded wick body, toward the other of the upper surface side and the opposite lower surface side of the porous molded wick body;
the heating element is disposed adjacent to the heat transfer element receiving side of the porous molded wick body; and
each of the plurality of heat transfer elements extends from the heating element into a corresponding recess to transfer heat from the heating element to porous molded wick body.

7. An anesthetic evaporator wick in accordance with claim 1, wherein;
the recesses extend downward in the vertical direction from the upper end of the porous molded wick body to a location spaced from the opposite lower surface side; and
each of the heat transfer elements extend downward from above the porous molded wick body into the respective one of the recesses.

8. An anesthetic evaporator comprising:
a wick comprising a porous molded wick body defining a plurality of air ducts passing through the molded wick body from an upper surface side to an opposite lower surface side and extending in a vertical direction in an installed position of the porous molded wick body, a plurality of upper deflection chambers which connect an upper area of two of the air ducts to one another, the upper deflection chambers being at least partially defined by the molded wick body and each being configured as a depression in the molded wick body top surface side; a plurality of lower deflection chambers which connect a lower area of two of the air ducts to one another, the lower deflection chambers being at least partially defined by the molded wick body and each being configured as a depression in the molded wick body bottom surface side and the porous molded wick body defining a plurality of recesses arranged between the air ducts;
a housing with an interior region that receives the wick;
an air inlet;
an air outlet, wherein the air inlet and the air outlet are arranged such that the air ducts and the upper deflection chambers and the lower deflection chambers form an air flow duct for gas to be enriched with anesthetic between the air inlet and the air outlet;
a plurality of heat transfer elements, wherein the heat transfer elements are each configured corresponding to one of the plurality of recesses defined by the molded wick body and extend into said one of the plurality of recesses defined by the molded wick body and mesh with said one of the plurality of recesses defined by the molded wick body to transfer heat from outside the wick body to within the wick body;
a heating element configured to generate heat; and
a temperature control/regulation element, the heating element being connected to the heat transfer elements for heating the heat transfer elements based on heating controlled by the temperature control/regulation element to heat the porous molded wick body.

9. An anesthetic evaporator in accordance with claim 8, wherein the housing has a pot component accommodating at least a lower section of the wick, the pot component cooperating with the lower deflection chambers to form a reservoir for liquid anesthetic with the lower deflection chambers.

10. An anesthetic evaporator in accordance with claim 8, wherein the housing has a cover component comprising the air inlet.

11. An anesthetic evaporator in accordance with claim 10, wherein the upper deflection chambers are at least partially defined by the cover component.

12. An anesthetic evaporator in accordance with claim 8, wherein:
the housing has a cover component comprising the air inlet and the air outlet;
the cover component includes or is connected, via a heat transfer contact connection, to the plurality of heat transfer elements;
the recesses extend downward in a vertical direction from the upper surface side, which is an upper end of the porous molded wick body, to a location spaced from the opposite lower surface side.

13. An anesthetic evaporator in accordance with claim 8, wherein:
the housing has a cover component comprising the air inlet and the air outlet; and
the cover component includes or is connected to the heating element and the temperature control/regulation element.

14. An anesthetic evaporator in accordance with claim 8, wherein the porous molded wick body is an integral single piece structure.

15. An anesthetic evaporator in accordance with claim 8, wherein:
the recesses extend from a heat transfer element receiving side of the porous molded wick body, which heat transfer element receiving side is defined by one of the upper surface side and the opposite lower surface side of the porous molded wick body, toward the other of the upper surface side and the opposite lower surface side of the porous molded wick body;
the heating element is disposed adjacent to the heat transfer element receiving side of the porous molded wick body; and
each of the plurality of heat transfer elements extends from the heating element into a corresponding recess to transfer heat from the heating element to porous molded wick body.

16. An anesthetic evaporator in accordance with claim 15, wherein;
the recesses extend downward in the vertical direction from the upper end of the porous molded wick body to a location spaced from the opposite lower surface side; and
each of the heat transfer elements extend downward from above the porous molded wick body into the respective one of the recesses.

17. An anesthetic evaporator wick comprising:
a plurality of heat transfer elements; and
a porous, sintered material, molded, single piece, wick body, formed of sintered material molded as an integral single piece structure with a defined shape, the wick body comprising:

a plurality of air ducts defined within the molded wick body and extending in a vertical direction, in an installed position of the porous molded wick body and passing through the molded wick body from an upper surface side to an opposite lower surface side;

a plurality of upper deflection chambers at least partially defined by the molded wick body and which connect an upper area of two of the air ducts to one another;

a plurality of lower deflection chambers at least partially defined by the molded wick body and which connect a lower area of two of the air ducts to one another; and a plurality of recesses defined within the molded wick body, with each of the recesses arranged between a set of the air ducts and not connected in the lower area to the first duct, the second duct or the third duct via the lower deflection chamber and not connected in the upper area to the first duct, the second duct or the third duct via the upper deflection chamber such that the molded wick body does not provide fluid communication between the recesses and the first duct, between the recesses and the second duct or between the recesses and the third duct, the recesses extending a distance from a heat transfer element receiving side defined by one of the upper surface side and the opposite lower surface side toward the other of the upper surface side and the opposite lower surface side to provide a plurality of heat transfer element receiving spaces, with each of the heat transfer element receiving spaces configured with a shape corresponding to one of the plurality of heat transfer elements to receive one of the plurality of heat transfer elements from the heat transfer element receiving side and with each of the heat transfer elements being shaped to contact an inner side wall of a respective one of the recesses.

18. An anesthetic evaporator wick in accordance with claim 17, wherein;

the recesses extend downward in the vertical direction from the upper end of the porous molded wick body to an end location spaced from the opposite lower surface side; and each of the heat transfer elements extend downward from above the porous molded wick body into the respective one of the recesses.

19. An anesthetic evaporator wick in accordance with claim 17, wherein the lower deflection chambers form at least one reservoir for liquid anesthetic and extends in the vertical direction at least over half the height of the porous molded wick body.

* * * * *